United States Patent [19]

König et al.

[11] Patent Number: 5,055,699

[45] Date of Patent: Oct. 8, 1991

[54] DEVICE FOR MEASURING THE REFRACTIVE INDEX OF A FLUID, IN PARTICULAR INTENDED FOR MEASURING THE DENSITY OF THAT FLUID OR THE CONCENTRATION OF A SUBSTANCE DISSOLVED IN THAT FLUID

[75] Inventors: Johan W. König, Noordwijk; Pieter M. Houpt, The Hague, both of Netherlands

[73] Assignee: Nederlandse Organisatie Voor Toegepastnatuurwetenschappelijk Onderzoek Tno, The Hague, Netherlands

[21] Appl. No.: 513,781

[22] Filed: Apr. 24, 1990

[30] Foreign Application Priority Data

Apr. 25, 1989 [NL] Netherlands ............... 8901039

[51] Int. Cl.$^5$ .................. G01N 21/49; G01N 21/41
[52] U.S. Cl. .................... 250/577; 250/903; 356/133
[58] Field of Search .......... 250/577, 907, 902, 903; 356/128, 132, 133, 135, 136

[56] References Cited

U.S. PATENT DOCUMENTS 3,311,014  3/1967  Witt et al. .................... 356/133
3,727,066  4/1973  Louderback et al. .......... 250/218

FOREIGN PATENT DOCUMENTS 0194732  9/1986  European Pat. Off. .
3617717  12/1987  Fed. Rep. of Germany .
3726412  2/1989  Fed. Rep. of Germany .

Primary Examiner—David C. Nelms
Assistant Examiner—LaCharles P. Keesee
Attorney, Agent, or Firm—Bachman & Lapointe

[57] ABSTRACT

In order to measure the refractive index of a fluid use is made of a rod (1) which projects into the fluid and has a refractive index which is slightly larger than that of the fluid. At the end which is not immersed in the fluid, the rod is provided with a light source (3) radiating into the rod and with a light detector (5). That part of the rod which is to be immersed in the fluid is partially surrounded by a casing which permits only total reflection of the light, while at the site of the part or parts of the rod not surrounded by the casing refracted light can, depending on the refractive index of the fluid, leak into the fluid. A casing which is stable against the corrosive action of an aggressive fluid, such as concentrated sulphuric acid in a battery, consists, according to the invention, of a layer (10), trapped in a transparent tube (8), of a medium which has a lower refractive index than the said rod, in particular gas or vacuum. In order to nullify the interfering action of hydrogen gas bubbles adhering to the rod, at least that part of the rod, projecting into the fluid, which is not surrounded by the casing can project into a holder (12), which below the rod, is provided with openings (13), a line (14) for supplying gas under pressure opening into the upper part of the holder.

8 Claims, 2 Drawing Sheets

DEVICE FOR MEASURING THE REFRACTIVE INDEX OF A FLUID, IN PARTICULAR INTENDED FOR MEASURING THE DENSITY OF THAT FLUID OR THE CONCENTRATION OF A SUBSTANCE DISSOLVED IN THAT FLUID

BACKGROUND OF THE INVENTION

The invention relates to a device for measuring the refractive index of a fluid, in particular intended for measuring the density of the fluid or the concentration of a substance dissolved in that fluid, comprising a rod which projects into the fluid and has a refractive index which is slightly larger than that of the fluid, which rod is provided, at the end not immersed in the fluid, with a light source which radiates into the rod and with a light detector, that part of the rod which is to be immersed in the fluid being partially surrounded by a casing which permits only total reflection of the light, while at the site of the part (or parts) of the rod not surrounded by said casing refracted light can, depending on the refractive index of the fluid, leak into the fluid.

A device of this type is known from Netherlands Patent Application No. 8500726.

In this known device the said casing consists of a reflecting gold layer. Contrary to expectations, it has been found that this gold layer is not resistant to the corrosive action of an aggressive fluid, such as concentrated sulphuric acid.

The aim of the invention is to overcome this drawback and for this purpose said casing consists of a layer, trapped in a transparent tube, of a medium which has a lower refractive index than said rod, in particular gas or vacuum.

Usually, a quartz tube will be used.

It is pointed out that German Offenlegungsschrift No. 3302089 discloses a device for measuring the refractive index of a fluid, said device comprising an optical fiber of small diameter to be immersed in the fluid, which fiber is provided, at the end not to be immersed in the fluid, with both a light source and a light detector. The angle of incidence of the light on the wall of the fiber will always be greater than the critical angle, so that the light can emerge only at the point of the part of the fiber which is to be immersed in the fluid. However, this point also serves to return some of the light by reflection. For this purpose, the point must be accurately ground, which is a costly operation. Moreover, the accuracy of the measurement will leave something to be desired because the light can leak away only over a very small part of the fiber, that is to say the ground point.

SUMMARY OF THE INVENTION

With the device according to the invention, the possibility exists for positioning a number of closed quartz tubes mutually spaced around the rod, so that the refractive index of the fluid, and thus the density, can be determined at various depths in the fluid.

In general, however, it suffices if only the free end section of the part of the rod to be immersed in the fluid is not surrounded by the said casing.

In order to counter loss of light, the point of said free end section has been given a round shape.

When the device is used for density measurements in a battery, a problem can arise because of the adhesion of hydrogen gas bubbles to the parts of the rod immersed in the battery fluid. These bubbles interfere in the density measurement. The hydrogen gas formed at the cathode of the battery dissolves in the fluid and when the latter is saturated gas bubbles form. This problem can be solved by inserting at least that section of the rod, projecting into the fluid, which is not provided with a casing into a holder which is provided with openings below the rod, a line for supplying a gas under pressure opening into the upper part of the holder.

By using the gas under pressure periodically to exert pressure and lower the fluid level within the holder to below the rod, hydrogen bubbles adhering to the rod are removed. The density of the fluid is measured immediately after the fluid level has risen again as a result of releasing the gas pressure. Concomitant advantages are that the fluid within the holder is periodically refreshed and that the holder protects the rod against damage. When the fluid level rises the gas above it must be able to escape; this could take place via the supply line which in that case is connected to the atmosphere via a control valve; in general, however, it is preferable to make an opening, which has a cross-section which is appreciably smaller than the cross-section of the collection of openings below the rod, in the upper section of the holder wall.

BRIEF DESCRIPTION OF THE DRAWINGS

The invention will now be illustrated further with reference to the figures, in which two illustrative embodiments are shown.

DETAILED DESCRIPTION

Figure 1:
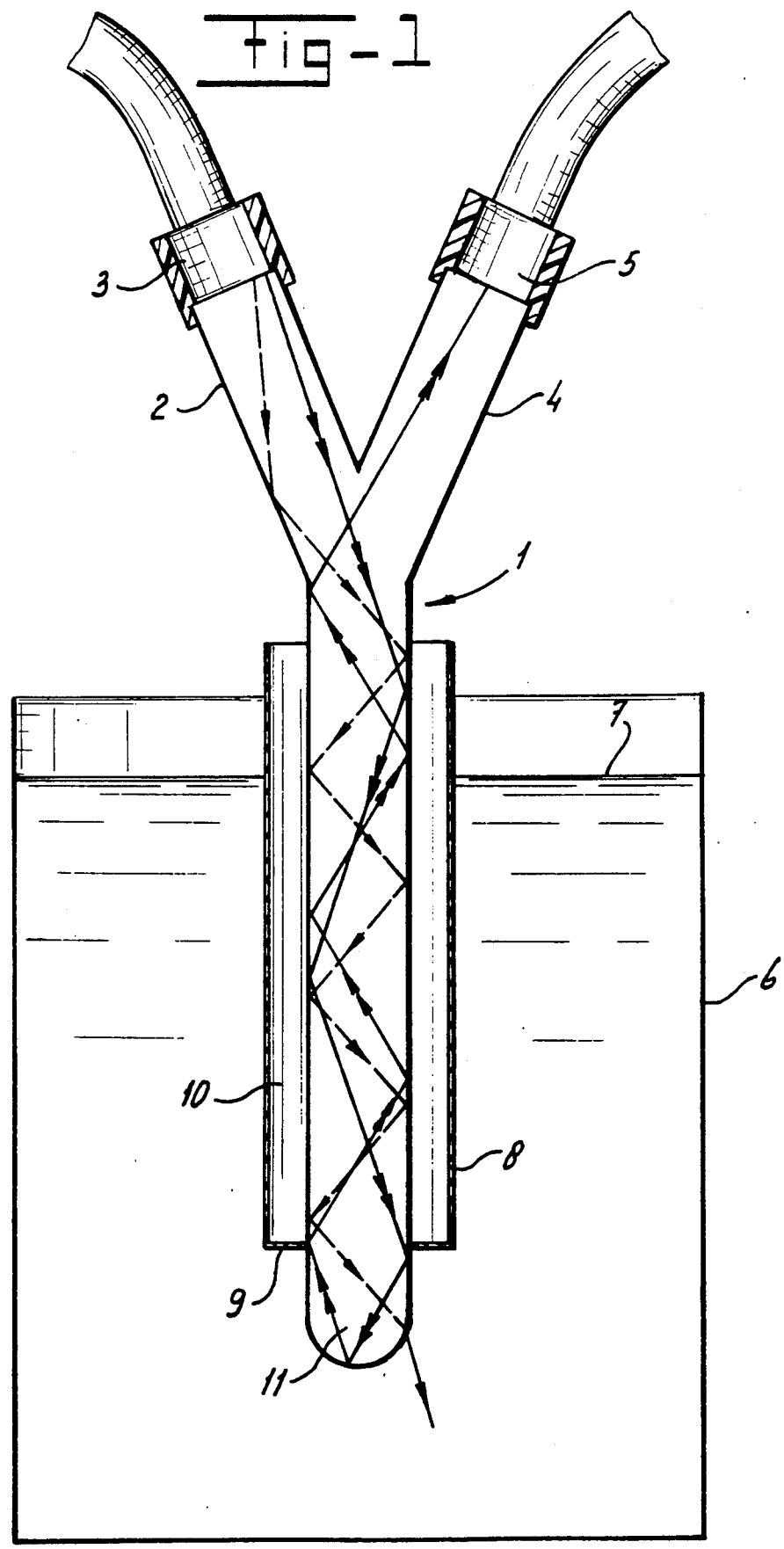
FIG. 1 is a sectional view of a first embodiment of the present invention.

The measuring device shown in the figures comprises a quartz rod 1 with a fork-shaped upper end. The diameter of the rod is, for example, 4 mm. A light source 3 for visible or invisible light is positioned on one leg 2 of the fork and a detector 5, which can convert light to electrical signals, is positioned on the other part 4 of the fork. The detector is connected to measuring equipment known per se.

The rod 1 is inserted in a trough 6 filled with fluid (for example a battery filled with concentrated sulphuric acid). The fluid level is indicated by 7.

A quartz tube 8 is attached around one section of that part of the rod which is not fork-shaped. This tube is connected by a base 9 to the rod 1 and is open at the top. There is a layer 10 of air between the rod wall and the wall of the quartz tube 8.

The free end of that part of the rod immersed in the fluid is rounded. It is shown how two light rays pass from the source 3 through the rod 1. At the quartz/air interface the angle of incidence is greater than the so-called critical angle, as a result of which total reflection occurs. At the bottom end 11 of the rod, the latter borders the fluid in the trough 6. If the angle of incidence at the site of the quartz/fluid interface is greater than the critical angle reflection will occur (see light ray indicated by double arrows) and if the angle of incidence at the site of said interface is smaller than the critical angle refraction will occur (see light ray indicated by single arrow). In the latter case light leaks away from the rod 1.

If the density of the fluid is relatively low, the refractive index of the fluid will also be relatively low, which leads to a small critical angle and a relatively large amount of reflection and little refraction. Relatively high density of the fluid leads to relatively little reflection and a large amount of refraction.

An appreciable part of the light which returns after reflection at the round end of part 11 will be incident on the detector 5. The magnitude of the electrical signal produced by this detector is a measure for the refractive index and thus for the density of the fluid in the trough 6 around the part 11.

The possibility exists for installing a number of closed quartz tubes mutually spaced around the rod 1, in which case light can leak away from the rod by means of refraction via the parts of the rod between the quartz tubes. In this case the density can be measured at various depths in the trough 6.

The essential feature for the inventive concept is that the rod 1 to be immersed in the fluid is, apart from the bottom end 11, not surrounded by a reflective gold layer but by a gas or vacuum.

The possibility exists for installing the legs 2 and 4 of the fork in a closed casing and to immerse the entire installation in the fluid. Moreover, the fork-shaped shaping of the rod is not essential. It would be possible to position the light source and the detector alongside one another in another way.

Figure 2:
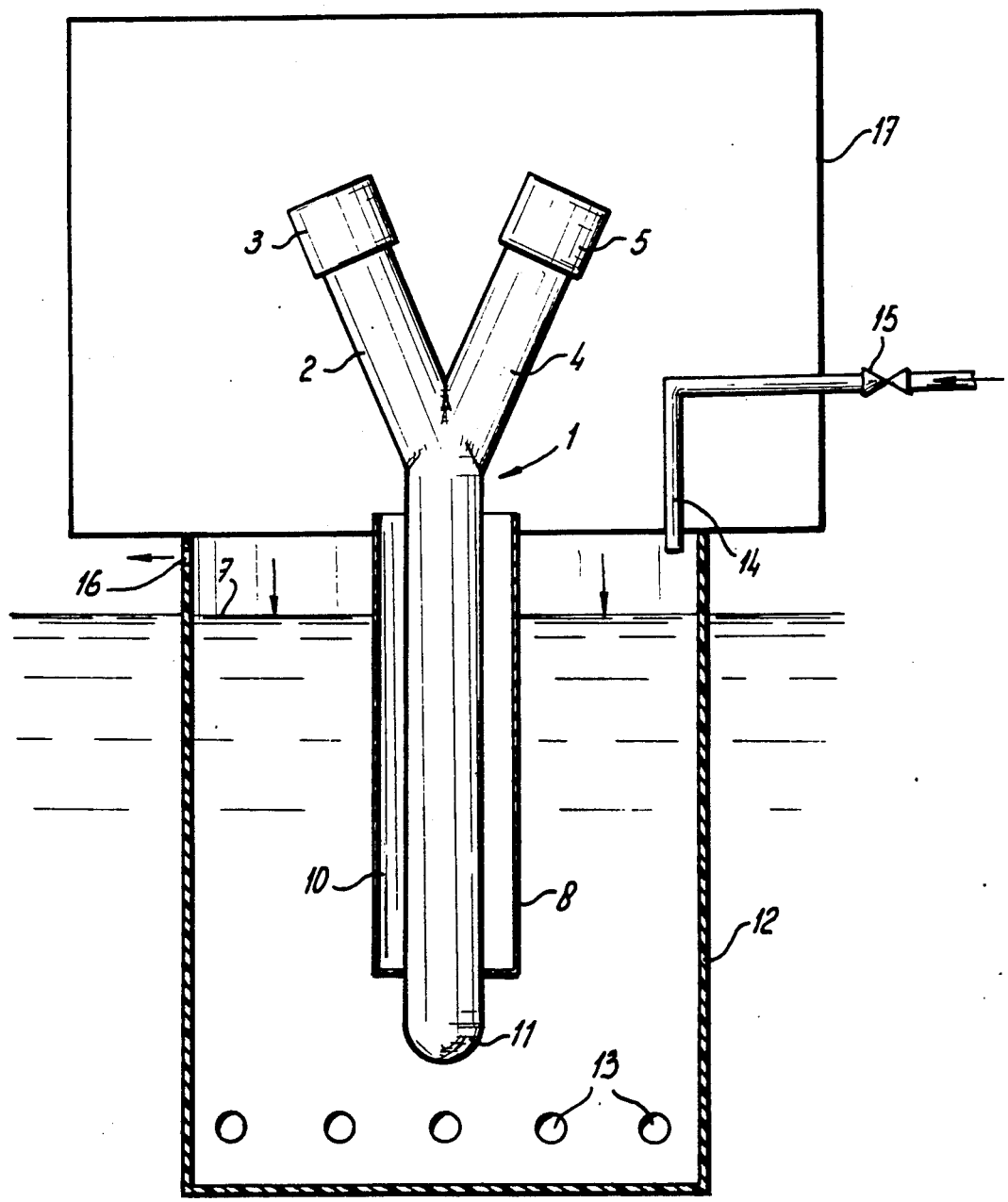
FIG. 2 is a sectional view of a second embodiment of the present invention.

The embodiment according to FIG. 2 differs from that according to FIG. 1 in that as the part of the rod 1 projecting into the fluid is fitted in a holder 12 which is provided at the bottom with a number of openings 13 and into which a line 14 with valve 15 opens at the top. Via this line a gas under pressure can be admitted to the holder 12 in order to cause the fluid level in the holder 12 to fall below the bottom of the rod just before a measurement. Hydrogen gas bubbles adhering to the rod, which have formed as a result of saturation of the fluid with hydrogen gas formed at the cathode of the battery, are removed by this means and the fluid in the holder is refreshed. The subsequent measurement is more accurate as a consequence. By closing the valve 15, the fluid level can rise again, the gas being able to escape from the holder via a narrow opening 16 close to the top edge of the holder. The holder 12 also has a protective function. The fork-shaped part of the rod is also placed in a small protective casing 17.

We claim:

1. Device for measuring the refractive index of a fluid, in particular intended for measuring the density of said fluid or the concentration of a substance dissolved in the fluid, comprising a rod having an end which projects into the fluid and has a refractive index which is slightly larger than that of the fluid, said rod being provided at the end not immersed in the fluid with a light source which radiates into the rod and with a light detector, wherein the part of the rod which is to be immersed in the fluid is partially surrounded by a casing which permits only total reflection of the light, while at the site of the rod to be immersed in the fluid and not surrounded by the casing refracted light can leak into the fluid depending on the refractive index of the fluid, and wherein the said casing consists of a layer trapped in a transparent tube, said layer being of a medium which has a lower refractive index than said rod.

2. Device according to claim 1 wherein said medium is a gas.

3. Device according to claim 1 wherein said medium is a vacuum.

4. Device according to claim 1 wherein said transparent tube is made of quartz.

5. Device according to claim 1 wherein the rod has a free end section to be immersed in the fluid and wherein only the free end section of the rod to be immersed in the fluid is not surrounded by the casing.

6. Device according to claim 5 wherein said free end section has a point and wherein the point of the free end section has a round shape.

7. Device according to claim 1 wherein at least that section of the rod projecting into the fluid which is not surrounded by the casing projects into a holder having an upper part, said holder being provided with openings below the rod, and a feed line for supplying gas under pressure opening into the upper part of the holder.

8. Device according to claim 7 wherein an opening which has a cross-section which is appreciably smaller than the cross-section of the openings below the rod is made in the upper part of the holder.

* * * * *